United States Patent
Ono et al.

(10) Patent No.: US 10,085,784 B2
(45) Date of Patent: Oct. 2, 2018

(54) BONE FIXING SCREW TEMPLATE AND METHOD FOR PRODUCING SAME

(75) Inventors: Hidenori Ono, Setagaya-ku (JP); Hisayuki Sugiyama, Setagaya-ku (JP)

(73) Assignee: ONO & CO., LTD., Tokyo (JP)

( * ) Notice: Subject to any disclaimer, the term of this patent is extended or adjusted under 35 U.S.C. 154(b) by 649 days.

(21) Appl. No.: 14/409,773

(22) PCT Filed: Jun. 25, 2012

(86) PCT No.: PCT/JP2012/066825
§ 371 (c)(1),
(2), (4) Date: Dec. 19, 2014

(87) PCT Pub. No.: WO2014/002284
PCT Pub. Date: Jan. 3, 2014

(65) Prior Publication Data
US 2015/0335371 A1   Nov. 26, 2015

(51) Int. Cl.
*A61B 17/88* (2006.01)
*A61B 17/70* (2006.01)
*A61B 17/17* (2006.01)
*A61B 17/56* (2006.01)

(52) U.S. Cl.
CPC ...... *A61B 17/8872* (2013.01); *A61B 17/1757* (2013.01); *A61B 17/7083* (2013.01); *A61B 2017/568* (2013.01)

(58) Field of Classification Search
CPC ............ A61B 17/1757; A61B 17/8872; A61B 17/7083; A61B 2017/568
See application file for complete search history.

(56) References Cited

U.S. PATENT DOCUMENTS

| | | | | |
|---|---|---|---|---|
| 3,108,500 A | * | 10/1963 | Merriman | B23B 49/023 408/115 B |
| 4,978,351 A | * | 12/1990 | Rozas | A61B 17/1725 606/102 |
| 5,423,826 A | | 6/1995 | Coates et al. | |
| 6,932,610 B2 | | 8/2005 | Ono et al. | |
| 8,359,118 B2 | | 1/2013 | Ono et al. | |

(Continued)

FOREIGN PATENT DOCUMENTS

| | | | | |
|---|---|---|---|---|
| EP | 2502582 A1 | * | 9/2012 | ......... A61B 17/1671 |
| JP | 9-504213 | | 4/1997 | |

(Continued)

*Primary Examiner* — Zade Coley
(74) *Attorney, Agent, or Firm* — Smith, Gambrell & Russell, LLP.

(57) ABSTRACT

A bone fixing screw template is a combination of: a template body (A) integrally constituted by a fitting section (1), which has an inner surface joining and fitting face-to-face to a three-dimensional-shaped surface of a bone region, and a cylindrical spacer tube guide cylinder (2) protruding while being pointed in a direction coaxial with the direction of insertion of the fitting section and a medical screw; and a cylindrical spacer tube (B) sliding in contact with the inner wall of the cylindrical spacer tube guide cylinder (2), the inner diameter of the cylindrical spacer tube (B) being formed to allow a drill to be slidable in the cylindrical spacer tube (B). By using the template, surgery requiring proficiency in fixing the bone region by tightening medical screws can be performed reliably and easily.

16 Claims, 5 Drawing Sheets

(56) References Cited

U.S. PATENT DOCUMENTS

| | | | |
|---|---|---|---|
| 2003/0023246 A1* | 1/2003 | Gotfried | A61B 17/1721 606/104 |
| 2006/0084986 A1* | 4/2006 | Grinberg | A61B 17/025 606/86 A |
| 2006/0093988 A1* | 5/2006 | Swaelens | A61C 13/0004 433/76 |
| 2007/0288030 A1* | 12/2007 | Metzger | A61B 17/154 606/87 |
| 2008/0287954 A1* | 11/2008 | Kunz | A61B 17/175 606/87 |
| 2011/0160772 A1* | 6/2011 | Arcenio | A61B 17/7053 606/248 |
| 2011/0238071 A1* | 9/2011 | Fernandez-Scoma | A61C 1/084 606/80 |
| 2011/0319745 A1* | 12/2011 | Frey | A61B 17/15 600/407 |
| 2012/0059362 A1 | 3/2012 | Ono | |
| 2012/0150242 A1* | 6/2012 | Mannion | A61B 17/1757 606/86 A |
| 2012/0245587 A1* | 9/2012 | Fang | A61B 17/1671 606/80 |
| 2013/0053854 A1* | 2/2013 | Schoenefeld | A61B 17/1757 606/87 |
| 2013/0116700 A1 | 5/2013 | Sugawara et al. | |
| 2013/0218163 A1* | 8/2013 | Frey | A61B 5/0488 606/87 |

FOREIGN PATENT DOCUMENTS

| | | |
|---|---|---|
| JP | 3927487 | 7/2004 |
| JP | 2009-61132 | 3/2009 |
| JP | 4423362 | 3/2009 |
| JP | 2009-273508 | 11/2009 |
| JP | 2010-264213 | 11/2010 |
| WO | 2011/149106 | 12/2011 |

* cited by examiner ately using a
fluoroscope, a bored hole in a predetermined direction, and
of a predetermined depth is formed by means of a drill, and
the spinal fusion screw is screwed into the bored hole to fix
the spine.

Accurate boring along the insertion direction from the
accurate position of insertion of the spinal fusion screw by
BONE FIXING SCREW TEMPLATE AND METHOD FOR PRODUCING SAME

TECHNICAL FIELD

This invention relates to a template for a bone fixing screw (hereinafter called a bone fixing screw template), and a method for producing the bone fixing screw template. In detail, if pain in the bone or intervertebral disk due to the deformation or degeneration of the bone associated with aging, or an external factor such as bone fracture or tumor, or pain, numbness, paralysis or excretory disorder accompanying dyskinesia of the upper part of the body or damage or compression of the nerve such as the spinal, cord or nerve root is not alleviated by conservative therapy, it is common practice to change the shape and position of the affected bone, thereby carrying out depressurization, or further perform surgery for fixing the bone by means of medical screws. In changing the shape of the bone, there is a case in which the bone at the site of nerve compression is shaven to eliminate the pressure on the compressed nerve, or a case where the shape deformed or crazed by aging or the external factor is resumed to the original shape. In changing the shape of the bone, moreover, other bone may be fixed to the diseased bone, or a reinforcing material may be applied to the diseased bone for fixation. For these bone shape changing surgeries, bone fixation by fastening medical screws is widely used.

The present invention relates to a bone fixing screw template useful for the prompt and reliable execution of a procedure in which a boring drill is operated at the position of insertion and in the direction of insertion of a medical screw to bore a hole, and the medical screw is screwed into the bored hole open in a predetermined direction, in surgery for fixing a diseased part of the bone by means of the medical screws tightened; a method for producing the bone fixing screw template; and a bone fixing screw template for use in a plan or exercise for the surgery.

BACKGROUND ART

Surgery for fixing a diseased part or lesion of the bone by tightening medical screws has so far been performed widely.

For a disease involving instability of the spine, such as spondylosis deformans or spinal injury, in particular, surgery for fixing the position of the spine by sticking medical screws made of titanium into the spine is widely performed.

This surgical technique, however, poses difficulty in ensuring the safety of the surgery sufficiently only with the use of the existing tool, because not only the shape of the bone itself, but the position of screw fixation and the path of sticking the screw are different according to a patient, symptoms and the contents of therapy.

With the surgery of spine fusion, therefore, injury to the blood vessel or nerve occurs when a spinal fusion screw is inserted into the spine, unless the site of insertion, the direction of insertion and the depth of insertion of the spinal fusion screw into the spine are strictly determined.

Currently, when a surgery using the spinal fusion screw is performed, the position, direction and depth of insertion of the spinal fusion screw are planned preoperatively using a fluoroscope, a bored hole in a predetermined direction, and of a predetermined depth is formed by means of a drill, and the spinal fusion screw is screwed into the bored hole to fix the spine.

Accurate boring along the insertion direction from the accurate position of insertion of the spinal fusion screw by use of this method, however, requires advanced skills. If boring is inaccurate, precise insertion of the spinal fusion screw into the spine is impossible. Even when the bored hole is formed correctly, it is likely for the medical screw to deviate from the planned path, if the medical screw fails to be screwed in from the correct direction after the boring procedure. If the predetermined diameter of the bored hole is large, in particular, a fine bored hole is first provided, and then a bored hole with a larger diameter is provided, with the fine hole being used as a guide. However, it involves great difficulty to bring the direction of the second drilling into exact conformity with the direction of the first drilling.

Patent Document 1 discloses a surgical method using a registration template for use in a medical navigation system-guided surgery.

With this surgical method, the position of the leading end of a medical instrument, such as a surgical knife or a drill, in an image of an operative site on a display is confirmed on the display, and surgery is performed, with knowledge of a state where the leading end of the medical instrument arrives at the correct position. The registration template is designed for such surgery, and is not a bone fixing template for setting the drilling position, direction and depth of the present invention precisely, and facilitating the screwing-in and tightening of a medical screw.

Patent Document 2 discloses a method for producing an artificial bone model which is manufactured by selective laser sintering to be described later, and which has cuttability closely resembling that of a natural bone.

Patent Document 3 discloses an instrument for treatment of a patient with impairment of the osseous semicircular canals, the instrument produced by use of a stereolithographic apparatus to be described later; and a method for manufacturing the instrument.

Patent Document 4 discloses a method for producing a soft blood vessel model for surgical simulation by use of ink-jet rapid prototyping to be described later.

PRIOR ART DOCUMENTS

Patent Documents

[Patent Document 1] Japanese Patent No. 4423362
[Patent Document 2] Japanese Patent. No. 3927487
[Patent Document 3] JP-A-2010-264213
[Patent Document 4] JP-A-2009-273508

DISCLOSURE OF THE INVENTION

Problems to be Solved by the Invention

It is an object of the present invention to provide a bone fixing screw template which facilitates the operation of providing a screw hole of a predetermined depth and a predetermined diameter from the accurate position of sticking in the direction of insertion of a medical screw, and screwing the medical screw into the screw hole, in surgery requiring advanced skills in fixing a bone by tightening the medical screw as stated previously; and a method for producing the bone fixing screw template.

Means for Solving the Problems

In an attempt to solve the above-described problems of the conventional technologies, the present inventors developed, in a pre-development stage, a method which comprises providing, in a direction coaxial with the direction of insertion, a through-hole having a diameter barely enough for accommodation of the diameter of a drill, at the position of sticking of a medical screw into a template having an intimately contacting inner surface accurately formed by an additive manufacturing technology or a layered manufacturing method using image processing; inserting the drill through the through-hole for drilling in the correct direction, and providing a bored hole of an accurate depth in the axial direction of the through-hole based on the distance between a mark on the surface of the drill shaft and the exit of the through-hole; then detaching the template; and then fastening the medical screw to the bone for fixation.

According to this method of the pre-development stage, however, the length of the through-hole determining the direction of the drill is so short that the direction of drill boring is likely to become away from the correct direction, thus potentially enlarging the bored hole in comparison with the diameter of the drill. According to the method, moreover, the diameter of the medical screw is larger than the diameter of the through-hole. Hence, the drawback is presented that the boring operation by the drill cannot be followed successively by the tightening of the medical screw, with the template being set in place. Before the tightening of the screw after detachment of the template, the state of the injured site may change. Furthermore, the screw tightening in the absence of a reference for directionality may entail the risk of the medical screw deviating from the planned path, because the bone is not as hard as a metal, thus erring in a bite of the screw thread. Besides, the screws are fixed, first on the right side, and then on the left side, or vice versa. Thus, a rotating force is exerted on the target site during surgery, so that the screw tends to be fixed in an outwardly escaping manner, thereby posing an increased danger of touching the nerve cord. In addition, if large holes are to be bored by two operations using drills of different diameters, there arises the need to replace the template in correspondence with the diameter of the drill. Replacement of the template takes time and, upon installation of another template, there is a possibility that the position and direction of the through-hole will deviate subtly, even when the intimately contacting inner surface is formed in exactly the same manner by the layered manufacturing method using image processing. Under these circumstances, it was found desirable, in the pre-development stage, to carry out the fixation of the bone with the medical screw, without detachment of the template, by a procedure ranging from a boring operation to a screw tightening operation.

In order to solve the problems of the conventional technologies and the problems in the pre-development stage, the present inventors first provided, in a sheet-shaped template, a cylindrical drill guide tube, which had an inner diameter larger than the maximum diameter of a medical screw, at the position of sticking of the medical screw in a direction coaxial with the direction of insertion, and then fitted a separately prepared cylindrical spacer tube into the cylindrical drill guide tube. By so doing, the present inventors found that the boring direction of the drill could be set accurately toward the axial direction of the cylindrical drill guide tube, and that the operation of tightening the medical screw could be performed continuously following the boring operation, without detachment of the template. Based on these findings, they have accomplished the present invention.

That is, the present invention provides the following:
(1) A bone fixing screw template for use in fixing a bone region by means of medical screws, the template comprising a template body and a cylindrical spacer tube, wherein the template body is integrally constituted by, a fitting section which has a three-dimensionally-shaped surface-joining/fitting inner surface to be joined and fitted face-to-face, in a male/female relationship, to a three-dimensionally-shaped surface of a bone region; and a 2 to 8 cm long cylindrical spacer tube guide cylinder communicating with an outside of the fitting section from the surface-joining/fitting inner surface of the fitting section; the cylindrical spacer tube guide cylinder protrudes at a position of insertion of the medical screw into the surface-joining/fitting inner surface of the fitting section, with a central axis of the cylindrical spacer tube guide cylinder being pointed in a direction coaxial with a direction of insertion of the medical screw, and the cylindrical spacer tube guide cylinder has an inner diameter 1.03 to 1.5 times a maximum outer diameter of the medical screw; and the cylindrical spacer tube is a cylindrical tube which has a length nearly identical with a length of the cylindrical spacer tube guide cylinder of the template body, which has an outer diameter identical with the inner diameter of the cylindrical spacer tube guide cylinder of the template such that the cylindrical spacer tube is slidable in the cylindrical spacer tube guide cylinder, and which has an inner diameter nearly identical with an outer diameter of a drill such that the drill is slidable in the cylindrical spacer tube.
(2) The bone fixing screw template according to (1), wherein the fitting section having the surface-joining/fitting inner surface of the template body is in a shape of a sheet; and the cylindrical spacer tube guide cylinder of the template body is a tubular cylinder protruding from an outer surface of the fitting section sheet.
(3) The bone fixing screw template according to (1) or (2), wherein a convex rib or a concave groove continuing in an identical cross-sectional shape from an inlet to an outlet of the cylindrical spacer tube guide cylinder is provided in an inner surface of the cylindrical spacer tube guide cylinder; and a concave groove or a convex rib continuing in an identical cross-sectional shape from a proximal end to a distal end of the cylindrical spacer tube and fitting to the convex rib or concave groove in the inner surface of the cylindrical spacer tube guide cylinder is provided in an outer surface of the cylindrical spacer tube.
(4) The bone fixing screw template according to any one of (1) to (3), wherein a detachable locking section is provided between a proximal end of the cylindrical spacer tube and an inlet portion of the cylindrical spacer tube guide cylinder of the template body.
(5) The bone fixing screw template according to any one of (1) to (4), wherein the template body is a body of a vertebral fixing screw template.
(6) The bone fixing screw template according to any one of (1) to (5), wherein the cylindrical spacer tube comprises the single cylindrical spacer tube, or comprises a combination of a plurality of the cylindrical spacer tubes with different inner diameters.
(7) The bone fixing screw template according to any one of (1) to (5), wherein the cylindrical spacer tube comprises a plurality of the cylindrical spacer tubes arranged in layers in contact with an inner wall of the cylindrical spacer tube guide cylinder.
(8) A method for producing the bone fixing screw template according to any one of (1) to (7), comprising: forming a shape of the surface-joining/fitting inner surface of the template body by a stereoscopic shaping device or a cutting device working interlockingly with three-dimensional shape data created from tomography information on a bone region of a patient.

(9) The method for producing the bone fixing screw template according to (8), comprising: preparing an actual-size stereomodel of the bone region of the patient by a stereoscopic shaping device working interlockingly with the three-dimensional shape data; providing the cylindrical spacer tube guide cylinder at a predetermined position of the stereomodel by temporarily fixing it while pointing it in a predetermined direction; pressing a curable inorganic material or a curable organic material in a predetermined area against a surface of the stereomodel around a lower end of the cylindrical spacer tube guide cylinder, thereby transferring a bone curved surface at a predetermined position of the model, as a template surface, to an inner surface of the curable inorganic material or the curable organic material; and then curing the bone curved surface-transferred curable inorganic material or curable organic material by drying, heating, irradiation with ultraviolet rays, or laser irradiation to prepare a cured template equipped with the cylindrical spacer tube guide cylinder.

(10) The method for producing the bone fixing screw template according to (8), comprising: using as an inner surface a stereoscopic surface shape based on stereoscopic surface image data created from data including a plurality of tomographic images of a bone at a surgery-targeted site of the patient; adding a predetermined wall thickness to the inner surface on a side opposite to a surface of the bone to create stereoscopic template shape data; adding, to the stereoscopic template shape data of the image data, shape data on the cylindrical spacer tube guide cylinder protruding from an inner surface of the stereoscopic surface shape, with a central axis of the cylindrical spacer tube guide cylinder being pointed in a direction coaxial with the direction of insertion of the medical screw, thereby forming data on a template body; and producing the template body by a shaping method using a stereoscopic shaping device, or a shaping method using a cutting device, each device working interlockingly with shape data on the template body.

(11) The method for producing the bone fixing screw template according to any one of (8) to (10), wherein the stereoscopic shaping device working interlockingly with the three-dimensional shape data is a selective laser sintering device which sinters and solidifies a resin powder or a metal powder by laser light, or a stereolithography device which cures a photosetting resin by laser light.

(12) A bone fixing screw template for use in a surgical plan or a surgical exercise, comprising a combination of the template body and the cylindrical spacer tube produced by the method for producing the bone fixing screw template according to any one of (8) to (11); and an actual-size stereomodel of the bone region of the patient further combined with the combination, the actual-size stereomodel being prepared by the stereoscopic shaping device working interlockingly with the three-dimensional shape data created from the tomography information on the bone region of the patient.

Effects of the Invention

The present invention is of effective in facilitating medical screw fixing surgery requiring proficiency.

Concretely, the invention has the following main effects:
1. By providing the cylindrical spacer tube guide cylinder, the position, direction and depth of a bored hole by means of a drill can be defined accurately as planned before surgery.
2. By providing the cylindrical spacer tube, a medical screw can be accurately screwed in after boring with the drill, simply by detaching the cylindrical spacer tube, without detaching the template body.
3. By readying a plurality of the cylindrical spacer tubes with different inner diameters, drills with different outer diameters can be used continuously, with the template being mounted on the bone lesion of the patient. That is, the occurrence of human errors can be minimized.
4. A three-piece set composed of an actual-size bone model combined with the template of the present invention can be used effectively in a simulation of or an exercise for surgery of the target lesion.
5. The template body is produced by a stereoscopic shaping method based on image information, whereby the fitting section having a three-dimensionally-shaped, very precise surface-joining/fitting inner surface can be formed.

Figure 1:
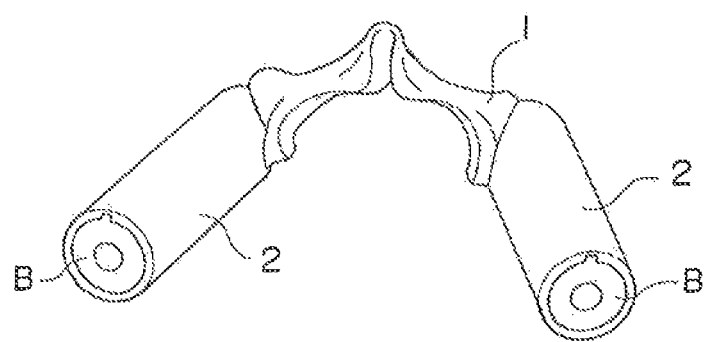
FIG. 1 is a perspective view, from a front direction, of an embodiment of a bone fixing screw template according to the present invention.

In the drawings, A denotes a template body, B denotes the cylindrical spacer tube, $B_1$ and $B_2$ denote the cylindrical spacer tubes as respective layers when the cylindrical spacer tubes are provided as two layers, H denotes an actual-size stereomodel of a vertebral bone region, M denotes a concave groove, L denotes a convex rib, 1 denotes a fitting section having a surface-joining/fitting inner surface, 2 denotes the cylindrical spacer tube guide cylinder, 3 denotes a drill insertion opening, R denotes a complementary curved surface, and E denotes the contour of the complementary curved surface.

BEST MODE FOR CARRYING OUT THE INVENTION

The material for the template of the present invention is a shapable plastic material. As the material, an organic substance or an inorganic substance can be used without limitation, as long as it has a certain strength.

The material for the template should desirably be one having moderate hardness, and should also desirably be one having biocompatibility. Examples of the one having biocompatibility are publicly known synthetic resins, rubbers, inorganic material, and inorganic powders which have already been known to be biocompatible, and composite materials composed of them. Moreover, sterilization, such as gas sterilization or coating, can be performed for the template.

If the template body of the present invention requires a surface which joins/fits particularly closely to a bone surface, it is desirable to produce the template body, or an actual-size stereomodel of a patient's bone region to whose surface the template is to be joined/fitted, the stereomodel being used as a die, by a 3D modeling (i.e., three-dimensional (3D) or stereoscopic shaping) apparatus or a cutting device which acts in association with shape data on the template body.

In this case, there can be used, as the material for the template body, a material suitable for a stereoscopic shaping apparatus, which acts interlockingly with the shape data, for example, an epoxy resin, an acrylic resin, or a metal such as titanium or stainless steel. As a shaping method which carries out shaping by inputting the shape data, any publicly known stereo image shaping method can be utilized without limitation, and its examples include stereoscopic shaping methods such as powder sintering additive manufacturing, stereolithography, ink-jet rapid prototyping, fused deposition modeling, laminated object manufacturing, and cutting additive manufacturing, and shaping methods such as the cutting method.

Of these methods, the powder sintering additive manufacturing, especially, selective laser sintering, and stereolithography, particularly, laser light stereolithography, and ink-jet rapid prototyping are desirable in that they can reproduce image data precisely.

As a shaping method for preparing the bone fixing screw template of the present invention by use of a metal, there can be named a metal/optical shaping combined processing method using a combination of rapid prototyping and cutting, a cutting method (a machining method generally called milling), and a casting process such as full mold casting or lost wax casting.

For an actual-size model of a patient's bone region, which is used in combination with the bone fixing screw template of the present invention for an exercise in surgery, it is desirable to shape an acrylic resin having cuttability similar to that of a natural bone by use of the ink-jet rapid prototyping method.

The material for the cylindrical spacer tube of the present invention may be a metal or organic matter, which can be used without limitation.

The present invention will now be described in detail with reference to the accompanying drawings.

Figure 2:
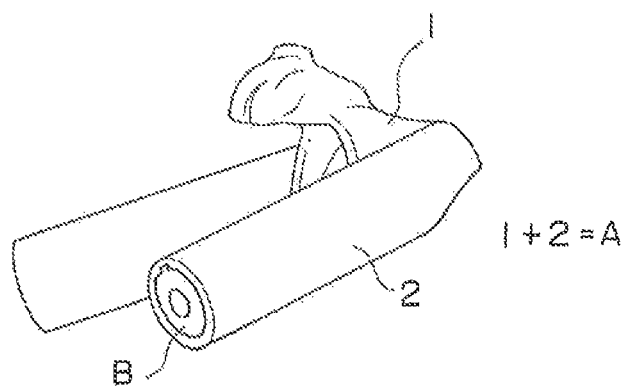
FIG. 2 is a perspective view, from a lateral direction, of the embodiment of the bone fixing screw template according to the present invention.

FIGS. 1 and 2 are views showing the use of the bone fixing screw template of the present invention as a spine fixing screw template which is an embodiment of the bone fixing screw template.

FIG. 1 is a perspective view, from a front direction, of a body A of the bone fixing screw template of the present invention. FIG. 2 is a perspective view, from a lateral direction, of the body A. The body A in these drawings corresponds to A in FIGS. 3 and 4.

Figure 3:
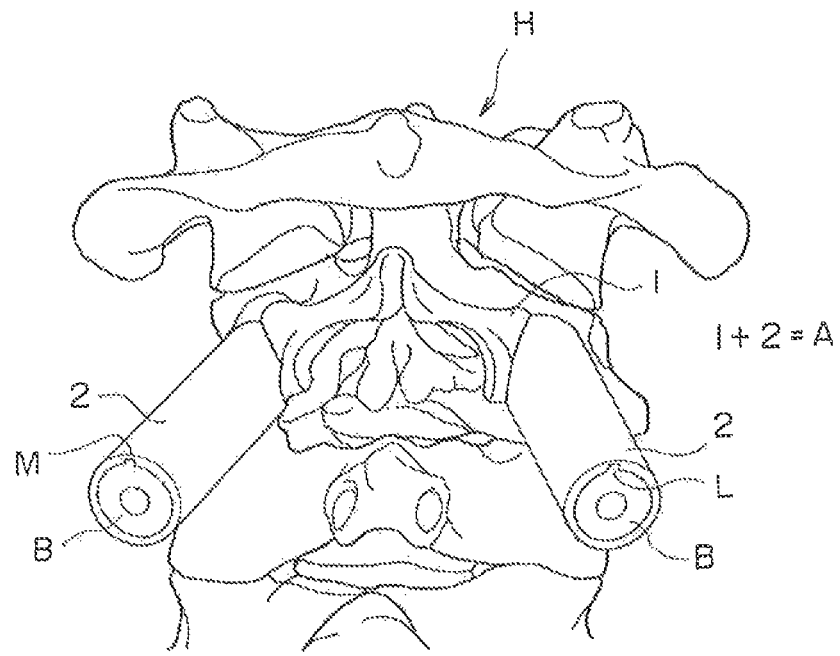
FIG. 3 is a perspective view, from a front direction, of a state in which the bone fixing screw template shown in FIGS. 1 and 2 has been fitted to an actual-size stereomodel of a vertebral region as an example of a diseased part or lesion.
Figure 4:
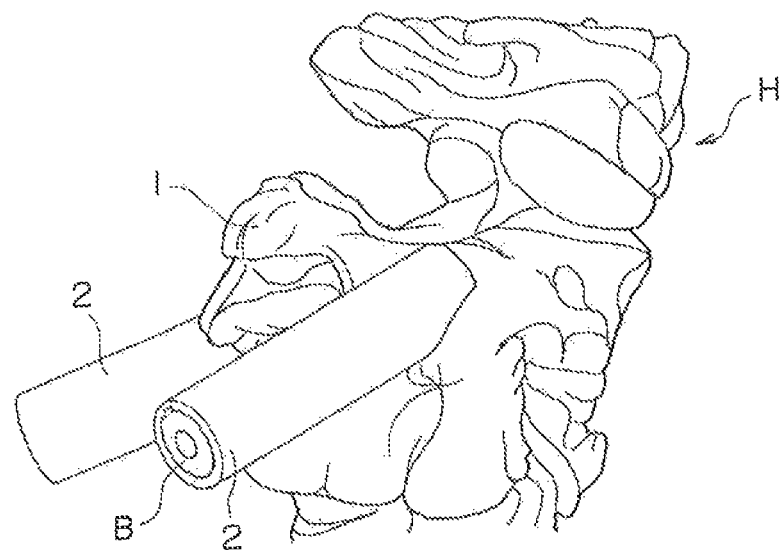
FIG. 4 is a perspective view, from a lateral direction, of the state in which the bone fixing screw template shown in FIGS. 1 and 2 has been fitted to the actual-size stereomodel of the vertebral region as the example of the lesion.

FIGS. 3 and 4 are a perspective view from a front direction (FIG. 3) and a perspective view from a lateral direction (FIG. 4), of a state in which the bone fixing screw template body A of the present invention has been joined and fitted, surface-to-surface, to an actual-size stereomodel H of a vertebral region as an example of a lesion. The actual-size stereomodel H of the vertebral region as one example of the lesion in FIGS. 3 and 4 can be prepared by the ink-jet rapid prototyping method whose execution is interlocked with three-dimensional shape data created from CT tomographic information on the vertebral region of the patient. A three-piece set consisting of the template body A, a cylindrical spacer tube B, and the actual-size stereomodel H of the vertebral region, shown in FIGS. 3 and 4, can be subjected to a preliminary exercise comprising an operation of fitting the template body A to the actual-size stereomodel H of the vertebral region; an operation of inserting the cylindrical spacer tube B into a cylindrical spacer tube guide cylinder 2 for fixation; an operation of inserting a drill into the cylindrical spacer tube F bore a hole; an operation of withdrawing the drill after boring, removing the cylindrical spacer tube B as well, and inserting a medical screw via the cylindrical spacer tube guide cylinder 2 to fasten the medical screw straight into the bored hole; and an operation of finally detaching the template body from the vertebral region. With the above three-piece set shown in FIGS. 3 and 4, moreover, the actual-size stereomodel of the patient's bone region and the template are combined so that a plan for surgery can be worked out stereoscopically using the model and the template before surgery is performed.

Furthermore, it can be finally checked whether the length and diameter of the cylindrical space tube guide cylinder 2 would not be a three-dimensional impediment to the fitting operation.

FIGS. 1, 2, 3 and 4 show the template body A, and the cylindrical spacer tube B inserted into the cylindrical spacer tube guide cylinder 2 of the template body A.

The template body A is composed of a fitting section 1, which has a 3D-shaped surface-joining/fitting inner surface joined and fitted face-to-face, in a male/female relationship, to the 3D-shaped surface of the actual-size stereomodel H of the vertebral region, and two of the 2 to 8 cm long cylindrical spacer tube guide cylinders 2 fixed to the right and left sides of the fitting section 1, the fitting section 1 and the cylindrical spacer tube guide cylinders 2 being provided integrally.

If the length of the cylindrical spacer tube guide cylinder 2 is short, there will be decreases in the precision of the boring direction of the drill and the operation of tightening the medical screw. If the length of the cylindrical spacer tube guide cylinder 2 is too great, no improvement will be made in directional accuracy corresponding to the increased length, and surgery will be stereoscopically impeded. There will also be difficulty with the operation of tightening the medical screw. The inner diameter of the cylindrical spacer tube guide cylinder 2 is 1.03 to 1.5 times, preferably 1.1 to 1.3 times, the maximum outer diameter of the medical screw. If the vertebral region is diseased, the inner diameter of the cylindrical spacer tube guide cylinder 2 is about 1 cm.

In FIGS. 3 and 4, the surface-joining/fitting inner surface of the fitting section 1 is joined and fitted, in a male-and-female relationship, to the surface of the actual-size stereomodel H of the vertebral region. The cylindrical spacer tube guide cylinder 2 protrudes, with its central axis being pointed in a direction coaxial with the direction of insertion of the medical screw. The interior of the cylindrical spacer tube guide cylinder 2 communicates with the outside of the fitting section 1, and opens, from the surface-joining/fitting inner surface of the fitting section 1. The cylindrical spacer tube B is a tube of a cylindrical shape which has nearly the same length as the length of the cylindrical spacer tube guide cylinder 2 of the template body, has nearly the same outer diameter as the inner diameter of the cylindrical spacer tube guide cylinder 2 of the template, and has nearly the same inner diameter as the outer diameter of the drill. If the lesion is the vertebral region, the above inner diameter is about 4 mm.

If the inner diameter of the cylindrical spacer tube guide cylinder 2 is not larger than the maximum outer diameter of the medical screw, it is impossible to perform the screwing-in of the medical screw without detaching the template. If the inner diameter of the cylindrical spacer tube guide cylinder 2 is less than 1.03 times the maximum outer diameter of the medical screw, the operation of screwing the medical screw into the bone through the cylindrical spacer tube guide cylinder 2 is difficult to perform. If the inner diameter of the cylindrical spacer tube guide cylinder 2 exceeds 1.5 times the maximum outer diameter of the medical screw, too, the ease of the screwing-in operation does not increase and, in addition, the screw cannot be supported from outside, so that there is a risk of a decreased fixing accuracy. Besides, the outer diameter of the cylindrical spacer tube guide cylinder 2 is so large that the entire template body becomes bulky, presenting an obstacle to the operation of fitting into the bone region.

The cylindrical spacer tube B is inserted into the cylindrical spacer tube guide cylinder 2, and has the same outer diameter as the inner diameter of the cylindrical spacer tube guide cylinder 2. The sameness in this case means that the clearance between the inserted cylindrical spacer tube B and the cylindrical spacer tube guide cylinder 2 cannot be confirmed visually, but the cylindrical spacer tube B can be slid and inserted into the cylindrical spacer tube guide cylinder 2. The cylindrical spacer tube B may be slidable in the direction of insertion, but is preferably not slidable in the direction of rotation.

The inner diameter of the cylindrical spacer tube B (inner diameter of a drill insertion opening 3) is nearly the same as the diameter of the drill, but the drill is in nearly the same diametrical relationship with the inner diameter of the drill insertion opening 3 of the cylindrical spacer tube B such that the drill is slidably insertible into the drill insertion opening 3. This state of being slidable over the inner surface of the cylindrical spacer tube B is preferably rendered an even more smoothly slidable state not only in the direction of insertion, but also in the direction of rotation, as compared with the above-mentioned relation between the outer diameter of the cylindrical spacer tube B and the inner diameter of the cylindrical spacer tube guide cylinder 2. Accordingly, the range of the sameness of the diameter is preferably slightly greater than that in the state of slidability on the outer diameter of the cylindrical spacer tube B. This is expressed, in the present invention, as nearly the same inner diameter as the drill diameter.

If the outer diameter and inner diameter of the cylindrical spacer tube B are not slidably identical with the inner diameter of the cylindrical spacer tube guide cylinder 2 and the diameter of the drill, respectively, the direction of insertion of the drill and the medical screw becomes unstable during the boring operation, resulting in inaccurate boring in connection with the diameter and direction of the bored hole.

If a bored hole of a small diameter is to be made, a single cylindrical spacer tube B is enough, if a bored hole of a large diameter is to be made, boring is sometimes performed in two or more stages. In this case, cylindrical spacer tubes composed of a combination of a plurality of the cylindrical spacer tubes with different inner diameters are used, or a plurality of the cylindrical spacer tubes arranged in layers in contact with the inner wall of the cylindrical spacer tube guide cylinder 2 are used. By so doing, boring can be performed promptly and accurately.

That is, if the cylindrical spacer tubes comprising the combination of the plurality of the cylindrical spacer tubes with different inner diameters are used, in second-stage boring, a drill having a larger diameter than the diameter of the drill in first-stage boring is used. If the cylindrical spacer tube B of the present invention is used in this case, two of the spacer tubes with different inner diameters are rendered ready for use. Thus, after completion of the first-stage boring, the cylindrical spacer tube B in the first stage is replaced by the one with a larger inner diameter. Simply by this measure, a large-diameter hole can be bored promptly by a continuous procedure, without laborious replacement of the template body.

Figure 9:
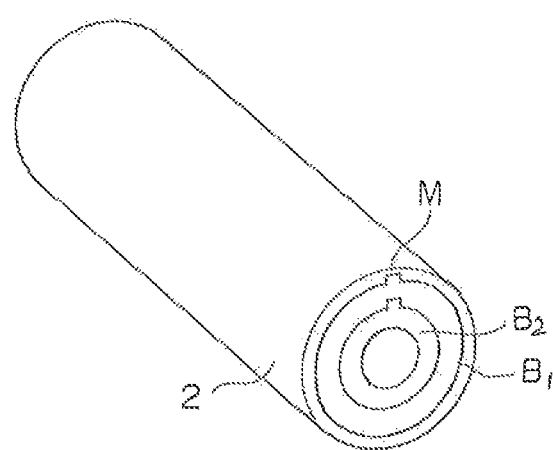
FIG. 9 is a perspective view showing a state in which two of the cylindrical spacer tubes, each representing one embodiment of the present invention, have been inserted in a double-layered configuration into the cylindrical spacer, tube guide cylinder.

If the plurality of the cylindrical spacer tubes inserted in layers through the cylindrical spacer tube guide cylinder 2 in contact therewith are used, for example, as illustrated in FIG. 9 showing the use of the cylindrical spacer tubes constituted in two layers, the relation between the outer diameter of the cylindrical spacer tube $B_1$ inserted through and contacted with the inside of the cylindrical spacer tube guide cylinder 2 and the inner diameter of the cylindrical spacer tube guide cylinder 2 is as described above and the cylindrical spacer tube $B_1$ needs to be slidable in the direction of insertion. The relation between the inner diameter of the cylindrical spacer tube $B_1$ inserted through and contacted with the inside of the cylindrical spacer tube guide cylinder 2 and the outer diameter of the cylindrical spacer tube $B_2$, as the next layer, inserted through and contacted with the inside of the cylindrical spacer tube $B_1$ is also similar to the above-mentioned relation, and the cylindrical spacer tube $B_2$ needs to be slidable in the direction of insertion, in this case, the inner diameter of the cylindrical spacer tube $B_2$ as the innermost layer, is nearly the same as the drill diameter, and the drill diameter is in such a nearly identical relation with the inner diameter of the drill insertion opening of the cylindrical spacer tube, as the innermost layer, that the drill is slidably insertible. This state of insertability over the inner surface of the cylindrical spacer tube $B_2$ as the innermost layer is preferably a state of even smoother slidability not only in the direction of rotation, but also in the direction of insertion, as compared with the aforementioned relation between the outer diameter of the cylindrical spacer tube B and the inner diameter of the cylindrical spacer tube guide cylinder 2. Therefore, the range of the sameness of the diameter is preferably slightly greater than that in the state of slidability on the outer surface of the cylindrical spacer tube $B_1$. In the present invention, this is expressed as nearly the same inner diameter as the drill diameter, as in the case of the one-layered cylindrical spacer tube. Here, the example of the cylindrical spacer tubes constituted as two layers is explained, but the same can be said of the cylindrical spacer tubes constituted in 3 or more layers. If the plurality of cylindrical spacer tubes inserted in layers through the cylindrical spacer tube guide cylinder 2 in contact with the inner wall thereof are used, it suffices to remove the cylindrical spacer tube as the innermost layer ($B_2$ in the case of the above two-layered configuration) after completion of the boring in the first stage. Simply by so doing, boring of a hole with a larger diameter in the next stage can be performed successively and promptly.

Replacement of the template body, on the other hand, takes time and labor, and also involves the risk that a subsequently bored hole in a replacement template may fail to be accurately coaxial with the previously bored hole, because the position of the bored hole in the replacement template is subtly out of order.

The template body in FIGS. 1, 2, 3 and 4 is an embodiment of the template body A of the present invention in which the fitting section 1 having the surface-joining fitting inner surface is sheet-shaped and the cylindrical spacer tube guide cylinder 2 of the template body is a tubular cylinder protruding from the external surface of the fitting section sheet.

Figure 5:
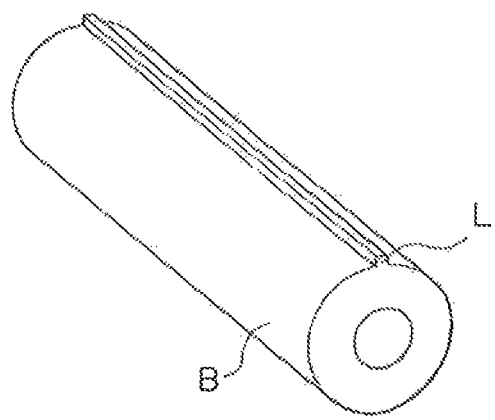
FIG. 5 is a perspective view of an embodiment of a cylindrical spacer tube according to the present invention.
Figure 6:
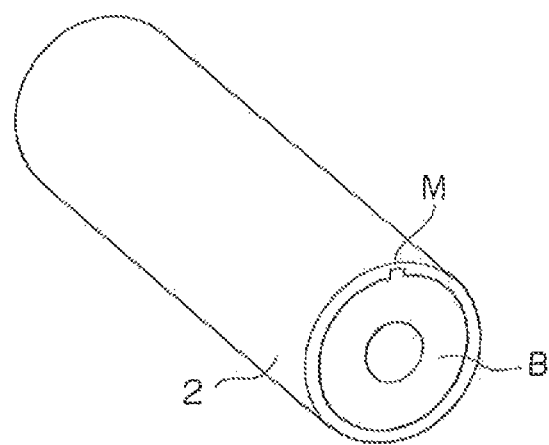
FIG. 6 is a perspective view of a state in which the cylindrical spacer tube as an embodiment of the present invention has been inserted into a cylindrical spacer tube guide cylinder.
Figure 7:
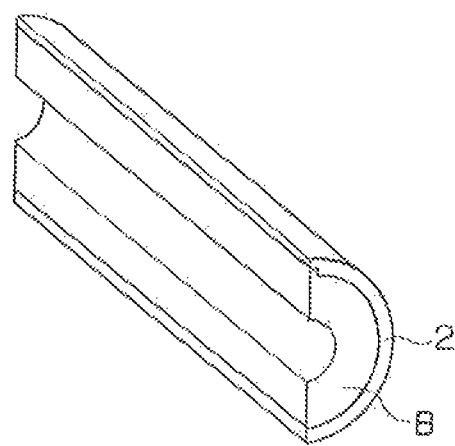
FIG. 7 is a perspective view of a longitudinally cut shape showing the internal structure of FIG. 6.

With the template of the present invention, as shown in FIGS. 5, 6 and 7, it is desirable that a concave groove M, which continues in the same cross-sectional shape from the inlet to the outlet of the cylindrical spacer tube guide cylinder 2 in a direction parallel to the direction of the length, be provided in the inner surface of the cylindrical spacer tube guide cylinder 2, and a convex rib L, which continues in the same cross-sectional shape from the proximal end to the distal end of the cylindrical spacer tube B and fits into the concave groove M of the cylindrical spacer tube guide cylinder 2, be provided in the outer surface of the cylindrical spacer tube B, whereby the cylindrical spacer tube B is prevented from rotating. It is also permissible to provide a convex rib, in place of the concave groove, in the inner surface of the cylindrical spacer tube guide cylinder 2, and provide a concave groove in the outer surface of the cylindrical spacer tube B. Alternatively, the concave groove and the convex rib are formed in a gently spiral shape, whereby the cylindrical spacer tube can be made not to slip off the cylindrical spacer tube guide cylinder in accordance with the motion of the drill. These alternative features can be applied to the relation between the inner surface of the cylindrical spacer tube as the outer layer and the outer surface of the cylindrical spacer tube as the layer inward thereof if the cylindrical spacer tubes are provided in two or more layers.

Figure 8:
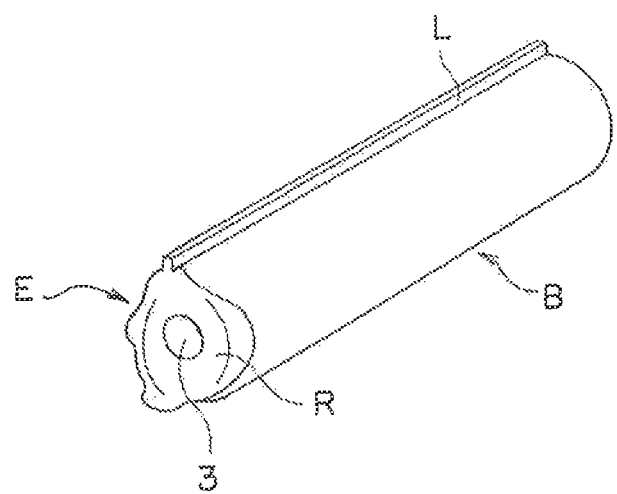
FIG. 8 is a perspective view of an embodiment of the cylindrical spacer tube of the present invention formed to have a leading end to be brought into surface contact with the shape of a bone surface.

By utilizing the concave groove and the convex rib, the cylindrical spacer tube B is inhibited from rotating. Thanks to this configuration, when the length of the cylindrical spacer tube B is set at exactly the same length as that of the cylindrical spacer tube guide cylinder 2, the shape of the leading end of the cylindrical spacer tube B is conformed to the curved shape of a bone surface which the leading end of the cylindrical spacer tube B contacts, as shown in FIG. 8. In this manner, the leading end of the cylindrical spacer tube B can be formed.

FIG. 8 is a view in which a complementary curved surface R to be brought complementarily into close contact with the curved-surface shape of a bone surface when the leading end of the cylindrical spacer tube B abuts on the bone surface is formed in the contour E of a thick-walled portion of the cylindrical spacer tube B.

With the template A of the present invention, it is desirable to provide a detachable locking section between the proximal end of the cylindrical spacer tube B and the inlet of the cylindrical spacer tube guide cylinder 2 of the template body. This measure can control the longitudinal movement of the cylindrical spacer tube B in the cylindrical spacer tube guide cylinder 2 in the boring operation of the drill.

As this means of locking, a means capable of performing temporary fastening can be used without limitation, such as by slightly increasing the diameter of the proximal end of the cylindrical spacer tube B; or providing a convex rib at the proximal end of the cylindrical spacer tube B, and engaging the convex rib with the groove in the inner surface of the cylindrical spacer tube guide cylinder 2, as if pushing a wedge into a pipe. Such a locking means can be applied between the cylindrical spacer tube as the outer layer and the cylindrical spacer tube as the layer inward thereof, if the cylindrical spacer tubes are provided in two or more layers.

The template of the present invention is preferred, because the shape of the surface-joining/fitting inner surface of the template body of the bone fixing screw template can be obtained as the fitting section having a three-dimensionally-shaped surface-joining/fitting inner surface joined and fitted to a 3D-shaped bone surface, in a male-and-female relationship, by precision production based on three-dimensional shape data created from CT tomographic information on a patient's bone region.

Two manufacturing methods are available for the above production based on three-dimensional shape data created from CT tomographic information on the bone region.

As the first of the methods, an actual-size stereomodel of a bone region of the patient, which is used as a die, is prepared by a stereoscopic shaping device interlocked with the above three-dimensional shape data, such as a selective laser sintering device, a stereolithography device, an ink-jet rapid prototyping device, a fused deposition modeling device, a laminated object manufacturing device, or a cutting additive manufacturing device, or a shaping device such as a cutting device. Then, the cylindrical spacer tube guide cylinder is temporarily fixed to a predetermined position of the stereomodel, and a curable inorganic material or a curable organic material is pressed in a sheet form against a predetermined area of the surface of the stereomodel around the lower end of the temporarily fixed cylindrical spacer tube guide cylinder, whereby a bone curved surface at the predetermined position of the model is transferred, as the template surface, to the inner surface of the curable inorganic material or the curable organic material. In the surroundings of the lower end of the temporarily fixed cylindrical spacer tube guide cylinder, the sheet-shaped curable inorganic material or curable organic material is desirably heaped up in the thickness direction to ensure the directionality of the cylindrical spacer tube guide cylinder. After transfer, the transferred sheet is cured by drying, heating, irradiation with ultraviolet ray, or laser irradiation. After curing, the cured template body equipped with the cylindrical spacer tube guide cylinder is separated from the stereomodel as the die, to manufacture the template body.

As the second method, a stereoscopic surface shape based on stereoscopic surface image data created from data including a plurality of tomography images of a bone at a surgery-targeted site of the patient is adopted as an inner surface, and a predetermined wall thickness is added to the inner surface on the side opposite to the bone surface to create stereoscopic template shape data. Then, editing is performed for adding, to the stereoscopic template shape data of the image data, shape data on the cylindrical spacer tube guide cylinder protruding from the inner surface of the stereoscopic surface shape data, with the central axis of the cylindrical spacer tube guide cylinder being directed in a direction coaxial with the direction of insertion of the medical screw, thereby forming stereoscopic shape data on the entire template body. Based on the resulting data, the template body is produced by a stereoscopic shaping device interlocked with the shape data on the template body, such as a selective laser sintering device, a stereolithography device, an ink-jet rapid prototyping device, a fused deposition modeling device, or a laminated object manufacturing device, or a shaping device such as a cutting device.

According to the above-mentioned second method in the present invention, the shape of a bone site in a human body, serving as a prototype, can be obtained by penetrative photographing or outline photographing using one of, or a combination of two or more of, magnetic resonance imaging (MRI), X-ray computed tomography (X-ray CT), and ultrasonic photographing. Image information from the actual human body can be applied to any of the above stereoscopic shaping devices or the cutting device interlocked with the stereoscopic shape data, for example, by converting a medical digital image into two-dimensional DICOM data, designing a 3D shape and a template by software, and further converting them into surface type STL format data.

In the manufacturing method of the present invention, bone site image information, which comprises the 3D shape of and dimensional data on a bone site of a human body as a prototype, is applied unchanged, whereby an actual-size stereomodel of the patient's bone region can be produced.

Then, shape information on a template in which the thickness of each site and a communicating cylindrical spacer tube guide cylinder are added to the opposite side of the stereo shape of the surface of the bone region with a predetermined wall thickness and area dimensions is applied to any of the above stereoscopic shaping devices or the shaping device such as the cutting device, working interlockingly with the shape data on the template body, whereby the template body can be produced.

As the manufacturing apparatus based on shape information on the template having a predetermined wall thickness and predetermined area dimensions in the present invention, there can be used, without limitation, a shaping device which, when receiving shape information, automatically creates a stereo shape as per the shape information in a manner interlocked with the shape information. For example, a rapid prototyping device (additive or layered manufacturing) working interlockingly with shape information is preferred. This method comprises first preparing the stereo shape of the template by software, and then outputting it in an STL format developed by 3D Systems, Inc, as a standard format of a shaping device. This format is processed into data on cross-sections sliced in thin layers on an NC machine. Based on the slice data, thin films are produced and stacked by any of the various shaping devices, so that a stereo shape as per image information can be layer-manufactured.

The shaping device usable is a stereoscopic shaping device, such as a selective laser sintering device, a stereolithography device, an ink-jet rapid prototyping device, a fused deposition modeling device, or a laminated object manufacturing device, or a shaping device such as a cutting device.

Of these devices, the selective laser sintering device, the stereolithography device, and the ink-jet rapid prototyping device are desirable in that they can reproduce the shape information accurately.

The selective laser sintering device used in the manufacturing method of the present invention is an additive manufacturing device which smoothes a powder material with a thin roller, and instantaneously sinters it with laser light, thereby stacking layers of the powder for shaping. This device is disclosed, for example, in Patent Document 2.

The stereolithography device used in the manufacturing method of the present invention is a shaping device relying on the most widely used rapid prototyping method in which a liquid photosetting resin is irradiated with an ultraviolet laser beam, whereby only its irradiated region is solidified for lamination. This device is disclosed, for example, in Patent Document 3.

The ink-jet rapid prototyping device used in the manufacturing method of the present invention is an additive manufacturing device which lets a binder out of an ink jet nozzle of a copier, adheres it mutually, and fix the adherends for lamination. This device is disclosed, for example, in Patent Document 4.

The fused deposition modeling device used in the manufacturing method of the present invention is an additive manufacturing device which heats a thermoplastic resin into a semi-liquid state, and extrudes the semi-liquid resin from a nozzle to cool and fix it for lamination.

The laminated object manufacturing device used in the manufacturing method of the present invention is an additive manufacturing device which cuts a sheet-shaped material such as paper with laser light or a cutting knife, and heats and adheres the cut materials together for lamination.

The ink-jet rapid prototyping device, in particular, is preferred for simulation before surgery for the following reasons: If a surgical target model of a patient to be prepared together with the template of the present invention, the model, when produced by the ink-jet rapid prototyping device using an acrylic resin as a shaping material, can become a stereoscopic actual-size model of the same hardness as that of a natural bone of a human body, the model being three-dimensionally duplicated precisely and accurately.

The stereolithography device is suitable when producing a transparent template using a transparent resin solution.

When the template of the present invention is to be prepared using a selective laser sintering device, a stereolithography device, an inkjet rapid prototyping device or the like, moreover, the use of a transparent material, such as a mere resin, as the starting material enables a transparent template body to be prepared. A transparent template is preferred, because the state of the surface of the bone to undergo surgery is easily visible using it.

In the present invention, a synthetic resin powder used as a material for the production of the template by use of the selective laser sintering device is not limited. Its examples are nylon, polycarbonate, polyester, polyacetal, polyethylene, polypropylene, polyvinyl chloride, polystyrene, polybutylene, ABS resin, cellulosic resin, acrylic resin, epoxy resin, and fluoroplastic. Of these materials, nylon can be used preferably, and nylon 11 can be used particularly preferably. No limitations are imposed on a photosetting resin for use as a material for the template in the stereolithography device and, for example, publicly known photosetting resins, such as acrylate resins or epoxy resins, can be used.

The use of a transparent material as a material for the template is preferred during operation, because when the template is brought into intimate contact with the patient's bone, the bone surface is visible.

The template in the present invention can be sterilized. As a sterilization treatment, gas sterilization or coating, for example, can be applied to the template.

EXAMPLES

Example 1

A template body composed of a fitting section, which had a 3D-shaped surface-joining/fitting inner surface joined and fitted face-to-face, in a male/female relationship, to the 3D-shaped surface of a vertebral region as a surgical target and, provided integrally with the fitting section, a 5 cm long cylindrical spacer tube guide cylinder communicating with the outside of the fitting section from the surface-joining/fitting inner surface of the fitting section was prepared by a stereolithography device using a photosetting resin.

Data on the template body conforming to the vertebral region of a lesion was created using the software "Mimics" (produced by Materialise) based on data from X-ray computed tomography of the vertebral region. To the data on the template, not only data on the thickness of the template body, but also data on the positions (directions), length, inner diameter and outer diameter of two of the cylindrical spacer tube guide cylinders were added.

The resulting data was inputted to the shaping device, by which an epoxy resin [trade name TSR-829, CMET Inc.] as a photosetting resin was sequentially laminated at a lamination pitch of 0.10 mm and cured to produce a template body A integrally having cylindrical spacer tube guide cylinders B with a maximum thickness of 15 mm to be fitted to the actual-size vertebral region. The smaller the lamination pitch, the better the template body coincides with the image shape. In the case of a bone fixing screw template, a lamination pitch of 0.10 mm or less is desirable.

Example 2

In the same manner as in Example 1, using shape data on the vertebral region of the same lesion obtained by X-ray computed tomography of the vertebral region, an actual-size acrylate resin stereomodel of the vertebral region of the lesion was prepared by an ink-jet rapid prototyping device. The ink-jet rapid prototyping device used was, a precis ion rapid prototyping machine "Eden500V" produced by Objet. Ltd. (modeling size 490 mm×390 mm×200 ram, mechanical dimensions 1320 mm×990 mm×1200 mm, lamination pitch 0.016 to 0.030 mm). As a modeling acrylate resin ink for the Objet Ltd.'s rapid prototyping machine, the ink "FuliCure 830 VeroWhite" produced by Objet Ltd., containing photoinitiator, was selected and used. The physical properties of a polymer prepared by photopolymerization of this ink, namely, the physical properties of the material for the bone model, are a tensile strength at break of 49.8 MPa, a tensile modulus of elasticity of 2495 Mpa, a flexural strength of 74.6, a flexural modulus of elasticity of 2137 MPa, an elongation of 15 to 25%, a Shore hardness of 83, a Rockwell hardness of 81, and a glass transition temperature of 58° C.

As a supporting material ink, a strippable, easily crushable water-soluble polyethylene glycol ink "FullCure 705" was selected from among supporting flexible resin inks dedicated to Objet Ltd.'s rapid prototyping machine, and used.

When the template body A was brought into contact with the surface of the constructed vertebral region model H, as shown in FIGS. 3 and 4, the surfaces of the two products were joined together with satisfactory accuracy, obtaining such a stable joint that the combined products were not displaced when shaken longitudinally and laterally.

The cylindrical spacer tube B was inserted into the cylindrical spacer tube guide cylinder 2 of the template body A, and stopped at the locking section. Then, a drill was inserted to bore the surface of the vertebral region model H to a predetermined depth. Then, the drill was pulled out, whereafter the cylindrical spacer tube B was removed. With the template body A being mounted, a medical screw was erected through the cylindrical spacer tube guide cylinder 2 straight on the bored hole, and the medical screw was screwed into the vertebral region of the model by means of a screwdriver.

During boring with the drill, a feeling that a bone was being bored was actually obtained. The template used for the preparatory exercise for surgery was used unchanged for an actual surgery to fix the vertebra by the medical screws.

Example 3

A template body composed of a fitting section, which had a 3D-shaped surface-joining/fitting inner surface joined and fitted face-to-face, in a male/female relationship, to the 3D-shaped surface of a vertebral region as a surgical target and, provided integrally with the fitting section, a 5 cm long cylindrical spacer tube guide cylinder communicating with the outside of the fitting section from the surface-joining/fitting inner surface of the fitting section was prepared by a 5-axis numerically controlled metal cutting device. Data on the template body conforming to the vertebral region was created using the software "Mimics" (produced by Materialise) based on data from X-ray computed tomography of the vertebral region of a lesion. To the data on the template, the thickness of the template body was added, and data on the positions (directions), length, inner diameter and outer diameter of two of the cylindrical spacer tube guide cylinders were also added.

The resulting data was inputted to a multi-tasking combined machining cutter [trade name "VARIAXIS 630", produced by Mazak Corporation], by which a titanium alloy, Ti-6Al-2Nb-1Ta, was used and cut at a cutting speed of 63 m/min and a precision of 30 to 0.50 μm to produce a template body A integrally having cylindrical spacer tube guide cylinders with a maximum thickness of 15 mm to be fitted to the actual-size vertebral region. The resulting template body A joined and fitted, with satisfactory precision, to the surface of the target vertebral region, thus obtaining a stable joint.

INDUSTRIAL APPLICABILITY

The template of the present invention can be utilized as a bone fixing screw template for medical screws, and utilized for a simulation model set for bone fixing surgery.

The invention claimed is:

1. A bone fixing screw template for use in fixing a bone region by means of medical screws and a drill, the template comprising a template body and a cylindrical spacer tube, wherein
the template body is integrally constituted by a fitting section which has a three-dimensionally-shaped surface-joining/fitting inner surface to be joined and fitted face-to-face, in a male/female relationship, to a three-dimensionally-shaped surface of a bone region, and a 2 to 8 cm long cylindrical spacer tube guide cylinder communicating with an outside of the fitting section from the surface-joining/fitting inner surface of the fitting section;
the cylindrical spacer tube guide cylinder protrudes at a position of insertion of a medical screw into the surface-joining/fitting inner surface of the fitting section, with a central axis of the cylindrical spacer tube guide cylinder being pointed in a direction coaxial with a direction of insertion of the medical screw;
the cylindrical spacer tube guide cylinder has an inner diameter 1.03 to 1.5 times a maximum outer diameter of the medical screw;

the cylindrical spacer tube is a cylindrical tube which has a length nearly identical with a length of the cylindrical spacer tube guide cylinder and an outer diameter identical with the inner diameter of the cylindrical spacer tube guide cylinder such that the cylindrical spacer tube is slidable in the cylindrical spacer tube guide cylinder;

the cylindrical spacer tube has an inner diameter nearly identical with an outer diameter of the drill such that the drill is slidable in the cylindrical spacer tube;

one of a convex rib or a concave groove continuing in an identical cross-sectional shape from an inlet to an outlet of the cylindrical spacer tube guide cylinder is provided in an inner surface of the cylindrical spacer tube guide cylinder, and another of a concave groove or a convex rib continuing in an identical cross-sectional shape from a proximal end to a distal end of the cylindrical spacer tube and fitting to one of the convex rib or concave groove in the inner surface of the cylindrical spacer tube guide cylinder is provided in an outer surface of the cylindrical spacer tube.

2. The bone fixing screw template according to claim 1, wherein
the fitting section having the surface-joining/fitting inner surface of the template body is in a shape of a sheet, and
the cylindrical spacer tube guide cylinder of the template body is a tubular cylinder protruding from an outer surface of the fitting section sheet.

3. The hone fixing screw template according to claim 1, wherein
a detachable locking section is provided between a proximal end of the cylindrical spacer tube and an inlet portion of the cylindrical spacer tube guide cylinder of the template body.

4. The bone fixing screw template according to claim 1, wherein
the template body is a body of a vertebral fixing screw template.

5. The bone fixing screw template according to claim 1, wherein
the cylindrical spacer tube comprises a single cylindrical spacer tube, or comprises a combination of a plurality of the cylindrical spacer tubes with different inner diameters.

6. The bone fixing screw template according to claim 1, wherein
the cylindrical spacer tube comprises a plurality of the cylindrical spacer tubes arranged in layers in contact with an inner of the cylindrical spacer tube guide cylinder.

7. A method for producing the bone fixing screw template according to claim 1, comprising:
forming a shape of the surface-joining/fitting inner surface of the template body by a stereoscopic shaping device or a cutting device working interlockingly with three-dimensional shape data created from tomography information on a bone region of a patient.

8. The method for producing the bone fixing screw template according to claim 7, comprising:
preparing an actual-size stereomodel of the bone region of the patient by a stereoscopic shaping device working interlockingly with the three-dimensional shape data;
providing the cylindrical spacer tube guide cylinder at a predetermined position of the stereomodel by temporarily fixing it while pointing it in a predetermined direction;
pressing a curable inorganic material or a curable organic material in a predetermined area against a surface of the stereomodel around a lower end of the cylindrical spacer tube guide cylinder, thereby transferring a bone curved surface at a predetermined position of the model, as a template surface, to an inner surface of the curable inorganic material or the curable organic material; and
then curing the bone curved surface-transferred curable inorganic material or curable organic material by drying, heating, irradiation with ultraviolet rays, or laser irradiation to prepare a cured template equipped with the cylindrical spacer tube guide cylinder.

9. The method for producing the bone fixing screw template according claim 8, wherein
the stereoscopic shaping device working interlockingly with the three-dimensional shape data is a selective laser sintering device which sinters and solidifies a resin powder or a metal powder by laser light, or a stereolithography device which cures a photosetting resin by laser light.

10. The method for producing the bone fixing screw template according to claim 7, comprising:
using as an inner surface a stereoscopic surface shape based on stereoscopic surface image data created from data including a plurality of tomographic images of a bone at a surgery-targeted site of the patient;
adding a predetermined wall thickness to the inner surface on a side opposite to a surface of the bone to create stereoscopic template shape data;
adding, to the stereoscopic template shape data of the image data, shape data on the cylindrical spacer tube guide cylinder protruding from an inner surface of the stereoscopic surface shape, with a central axis of the cylindrical spacer tube guide cylinder being pointed in a direction coaxial with the direction of insertion of the medical screw, thereby forming data on a template body; and
producing the template body by a shaping method using a stereoscopic shaping device, or a shaping method using a cutting device, each device working interlockingly with shape data on the template body.

11. The method for producing the bone fixing screw template according claim 10, wherein
the stereoscopic shaping device working interlockingly with the three-dimensional shape data is a selective laser sintering device which sinters and solidifies a resin powder or a metal powder by laser light, or a stereolithography device which cures a photosetting resin by laser light.

12. The method for producing the bone fixing screw template according to claim 7, wherein
the stereoscopic shaping device working interlockingly with the three-dimensional shape data is a selective laser sintering device which sinters and solidifies a resin powder or a metal powder by laser light, or a stereolithography device which cures a photosetting resin by laser light.

13. A bone fixing screw template for use in a surgical plan or a surgical exercise, comprising:
a combination of the template body and the cylindrical spacer tube according to claim 1 and produced by forming a shape of the surface-joining/fitting inner surface of the template body by a stereoscopic shaping device or a cutting device working interlockingly with three-dimensional shape data created from tomography information on a bone region of a patient; and an actual-size stereomodel of the bone region of the patient further combined with the combination, the actual-size stereomodel being prepared by the stereoscopic shaping device working interlockingly with the three-dimensional shape data created from the tomography information on the bone region of the patient.

14. A bone fixing screw template for use in a surgical plan or a surgical exercise, comprising:

a combination of the template body and the cylindrical spacer tube produced by the method for producing the bone fixing screw template according to claim 8; and an actual-size stereomodel of the bone region of the patient further combined with the combination, the actual-size stereomodel being prepared by the stereoscopic shaping device working interlockingly with the three-dimensional shape data created from the tomography information on the bone region of the patient.

15. A bone fixing screw template for use in a surgical plan or a surgical exercise, comprising:

a combination of the template body and the cylindrical spacer tube produced by the method for producing the bone fixing screw template according to claim 10; and an actual-size stereomodel of the bone region of the patient further combined with the combination, the actual-size stereomodel being prepared by the stereoscopic shaping device working interlockingly with the three-dimensional shape data created from the tomography information on the bone region of the patient.

16. A bone fixing screw template for use in a surgical plan or a surgical exercise, comprising:

a combination of the template body and the cylindrical spacer tube produced by the method for producing the bone fixing screw template according to claim 12; and an actual-size stereomodel of the bone region of the patient further combined with the combination, the actual-size stereomodel being prepared by the stereoscopic shaping device working interlockingly with the three-dimensional shape data created from the tomography information on the bone region of the patient.

* * * * *